United States Patent [19]

Bachelder et al.

[11] Patent Number: 4,928,533
[45] Date of Patent: May 29, 1990

[54] BURST TESTING APPARATUS

[75] Inventors: Walter F. Bachelder, Salonga; John L. Sullivan, Kings Park; Peter J. Fiore, Mt. Sinai; Godfrey L. Hansen, Amityville, all of N.Y.

[73] Assignee: Testing Machines Inc., Amityville, N.Y.

[21] Appl. No.: 374,480

[22] Filed: Jun. 30, 1989

[51] Int. Cl.⁵ .............................................. G01N 3/00
[52] U.S. Cl. ..................................................... 73/838
[58] Field of Search ................................ 73/838–840, 73/159; 162/263

[56] References Cited

U.S. PATENT DOCUMENTS

| | | | |
|---|---|---|---|
| 377,361 | 1/1988 | Mill | 73/840 |
| 3,160,002 | 12/1964 | Lovette | 73/840 |
| 3,600,940 | 8/1971 | Schlegel | 73/840 |

Primary Examiner—Robert Raevis
Attorney, Agent, or Firm—Anthony J. Casella; Gerald E. Hespos

[57] ABSTRACT

A burst testing apparatus is provided. The apparatus includes a burst tester for determining the burst strength of sheet material such as paper. An automatic feeder is provided for advancing the sheet material after each successive test. A photo-optical sensing means may also be provided for sensing the presence of the sheet material and for initiating a test. A control unit is operatively connected to the burst tester and the feeder. The control unit is operative to store and analyze burst test results.

11 Claims, 3 Drawing Sheets

BURST TESTING APPARATUS

BACKGROUND OF THE INVENTION

The subject invention is directed to an apparatus and method for testing the burst strength of sheet material, such as paper.

Sheet material, such as paper, is manufactured in complex automated processes to achieve specified characteristics in accordance with the intended end use of the product. For example, sheet material may be produced to have a specified thickness, weight, surface texture and strength. The sheet may be a single integral ply or may be laminated from different materials. It is necessary to check the paper or other such sheet material being produced by the automated machinery to ensure that it complies with specifications. Generally a plurality of tests are conducted on the sheet material from each production run of such material. The plurality of tests are then averaged, compared and/or otherwise analyzed to assess compliance with specifications.

Burst strength is a parameter that is typically used to assess the strength of paper and other such sheet material. The typical prior art apparatus for testing burst strength comprises upper and lower platens each of which has a central aperture therein. The platens of the prior art apparatus are selectively movable toward and away from one another to enable placement of the test material therebetween. More particularly, the typical prior art burst testing apparatus includes a manual screw clamp which enables clamping pressure to be exerted by the upper platen of the prior art apparatus to clamp a product sample under test between the two platens. The prior art burst test apparatus further includes an expandable diaphragm mounted below the central aperture in the lower platen. A hydraulic pump is in communication with the expandable diaphragm, and is operative to direct hydraulic fluid at a specified and controlled rate toward the diaphragm. The hydraulic pressure causes the diaphragm to expand through the apertures in the platens and eventually to burst the sheet material clamped therebetween. The prior art burst testing apparatus further includes a gauge which measures the hydraulic pressure required to burst the sheet material being tested. The above described prior art apparatus is described, for example, in the publication entitled "PERKIN'S TESTERS" which was published by B. F. Perkins Company in 1983.

As noted above, the prior art burst testers are employed by subjecting the sheet material sequentially to a plurality of different tests. To perform this plurality of tests, an operator manually advances the sheet material through the prior art apparatus to selected locations at which the tests are sequentially performed. For example, a typical sample of material to be tested might be a narrow 5-15 foot long sheet, with some 20-40 tests being performed at linearly spaced apart locations along the length of the sheet of test material. The operator of the prior art apparatus will manually position and clamp the sheet, initiate each test and manually move the sheet material linearly intermediate successive tests. In other situations tests will be performed at a plurality of locations about the perimeter of a rectangular sheet. In these situations the operator again will manually initiate tests and translate the sheet of material intermediate successive tests.

The prior art apparatus for burst testing sheet material is considered to have several significant deficiencies. For example, the typical prior art apparatus requires the clamping pressure of the platens to be manually applied. This manual application of clamping pressure inherently creates the possibly of errors and differences between tests. A loosely clamped sheet of material can yield significantly higher burst strength requirements than a tightly clamped sheet of material.

Many prior art burst testers use a dial gauge for recording the burst pressure. Dial gauges are inherently inaccurate during either low burst pressure testing or high burst pressure testing. Under low burst pressure testing, the relatively rapid increase in pressure can cause the gauge to lag significantly behind the actual pressure being applied. With high burst pressure testing, a definite pop and associated vibration occur when the sheet material bursts, such that the pressure sensor is subjected to vibration and shock that can cause an incorrect reading on the dial gauge.

Prior art burst testers also do not automatically terminate the flow of hydraulic fluid after the burst has occurred. Rather, the operator of the prior art apparatus may be required to manually terminate the testing procedure. Ideally, the operator should react quickly to the audible pop generated at the instant the sheet material bursts. However, there is often a lag between the burst and the termination of the flow of hydraulic fluid. This increased flow of hydraulic fluid after the completion of the test will significantly shorten the life of the diaphragm, and in some instances will yield inaccurate pressure gauge readings.

As noted above, the prior art burst testers require the operator to manually advance the sheet material through the prior art burst tester between successive tests. If the sheet material is advanced too far, the operator will waste the test material. If the sheet material is advanced insufficiently, the operator will perform overlapping tests with the later test being meaningless or misleading.

In addition to the above described deficiencies, the prior art apparatus is very time consuming and requires the full attention of the operator. Thus, the prior art burst testing apparatus necessarily results in high labor costs and prevents the test operator from performing other necessary tasks at the testing facility.

In view of the above, it is an object of the subject invention to provide an automated burst testing apparatus that automatically provides a selected clamping pressure against the material being tested and that relieves the clamping pressure at the end of the test.

It is another object of the subject invention to provide a burst tester that can feed the sheet material being tested from one test to the next sequential test location on the sheet material.

It is an additional object of the subject invention to provide a burst tester with actuation means for automatically initiating a test when the sheet material is in a selected position.

A further object of the subject invention is to provide a burst tester that is operative to feed test material of different thicknesses.

Still another object of the subject invention is to provide a burst tester that is operative to terminate the flow of hydraulic fluid substantially at the instant of the burst.

SUMMARY OF THE INVENTION

The subject invention is directed to an automatic testing apparatus having a burst tester and a control means for controlling the operation of the apparatus. The automatic testing apparatus may further comprise advancing means for advancing sheet material, sensing means for sensing the presence of the sheet material and printing means for printing test data. The burst tester includes a pair of opposed platens with central through apertures extending therethrough and generally in register with one another. The platens are selectively movable toward and away from one another to clamp a sheet of material therebetween.

The burst tester preferably comprises automatic clamping means for moving the platens toward one another to exert a selected pressure on the sheet material being tested. The automatic clamping means may be actuated by an operator or may be actuated in response to a signal generated by the testing apparatus. For example, the above identified sensing means may sense the presence of the sheet material at a location for performing a test thereon and thus may generate a signal to actuate the clamping means. The sensing means may comprise photo optical means for sensing the presence of the sheet material. Alternatively, or additionally, the signal to actuate the clamping means may be generated by the above identified feed or advancing means, such that the clamping means will automatically clamp the sheet material after the sheet material has been advanced a selected distance. The clamping means may also be operative to automatically release the sheet material after the completion of each burst test.

The burst tester further comprises an expandable diaphragm and a supply of hydraulic fluid in communication with the diaphragm. The testing apparatus is operative to direct hydraulic fluid toward the diaphragm after the sheet has been clamped between the platens. The hydraulic fluid while expand the diaphragm through the apertures in the platens and eventually burst the sheet clamped therebetween. The burst pressure is recorded by the testing apparatus for analysis, and the hydraulic pressure is released automatically after the burst.

The advancing means of the testing apparatus may comprise a pair of generally parallel rollers. At least one of the rollers may be rotatably driven by the testing apparatus. The drive roller may be disposed to be gravitationally below the sheet of material being tested. The other roller may be a weighted follower roller which is operative to exert a gravitational force on the sheet of material to urge the sheet of material against the drive roller. The follower roller may have a hinged or other movable connection to the testing apparatus to accommodate sheet material of varying thicknesses, and to be readily rotated out of the way for tests that do not require automatic feeding by the testing apparatus.

The control means of the testing apparatus preferably incorporates or is operatively connected to computing means and printing means for recording the test data, peforming basic arithmetic analysis on the test data and preparing a printed report of the test results. The computing means may also be operative to permit entry of other test data, such as the identity of the operator, the identity of the test sample, the date, time, temperature and humidity conditions.

DETAILED DESCRIPTION OF THE PREFERRED EMBODIMENT

Figure 1:
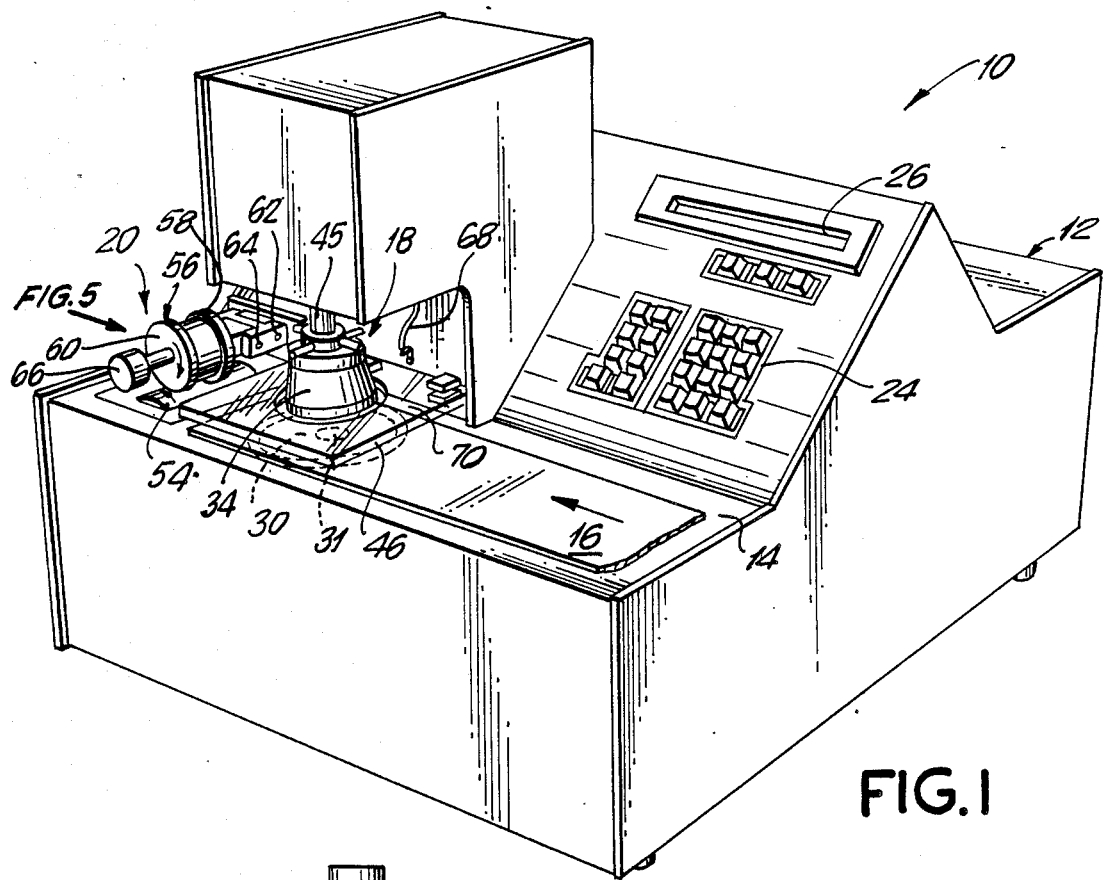
FIG. 1 is a perspective view of a testing apparatus in accordance with the subject invention.

The burst testing apparatus of the subject invention is identified generally by the numeral 10 in FIG. 1–4. The burst testing apparatus 10 comprises a housing 12 having a sheet supporting surface 14 for supporting a sheet 16 to be tested. The apparatus 10 further includes a burst tester 18 and a sheet feeder 20 both of which are in proximity to the sheet supporting surface 14.

Figure 3:
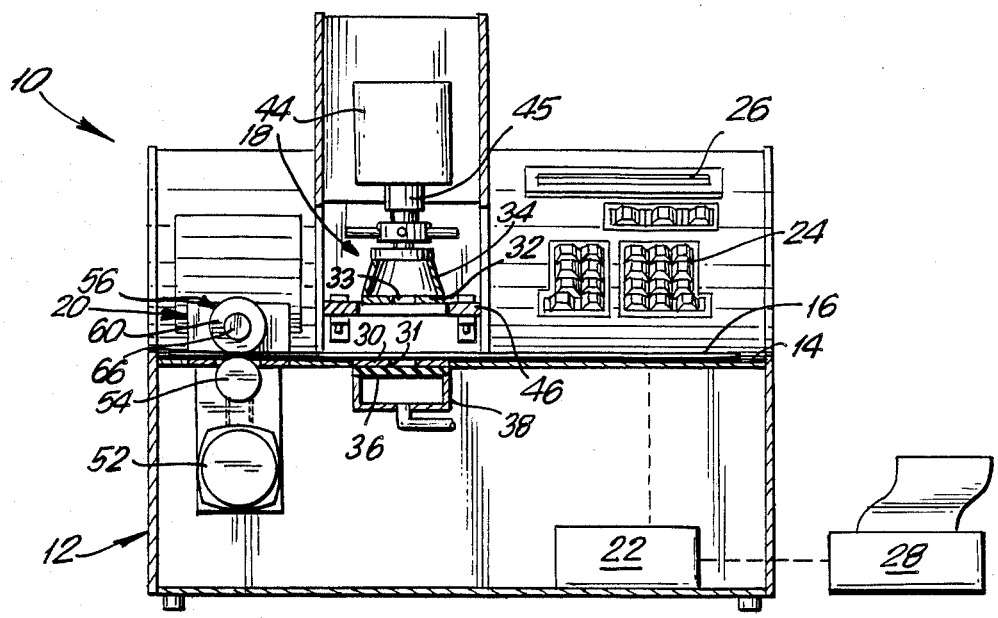
FIG. 3 is a front elevational view, partly in section, of a testing apparatus in accordance with the subject invention.

A control unit 22 is disposed within the housing 12 as shown in FIG. 3. An array of input controls 24 and a digital display screen 26 are mounted to the housing 12, and are operatively connected to the control unit 22. The burst testing apparatus 10 may further be operatively connected to a printer 28, as shown in FIG. 3. As depicted in FIG. 3, the printer 28 is disposed at an off-line location. However, in certain embodiments, the printer 28 may be incorporated into the housing 12 of the burst testing apparatus 10. The input controls 24 are employed to enter data into the control unit 22. In particular, the data entered through the input controls 24 may include the identity of the operator performing a test on the burst testing apparatus 10, the identity of the test sample 16 and various test conditions or parameters. The input controls 24 also enable the initiation of a test and the display or printing of test results. The display screen 26 is operative to display operator instructions, to prompt additionally input and to display at least selected test results. The control unit 22 may be any one of known microprocessors that enables the performance of computations based on data entered through the input controls 24 and based on test results as explained further herein.

The burst testing apparatus 10 comprises a lower platen 30 incorporated into the sheet supporting surface 14 and including a circular through aperture 31 extending therethrough. An upper platen 32 having a central through aperture 33 is disposed above the lower platen 30 such that the respective apertures 33 and 31 are in register with one another. An enclosed chamber 34 is securely mounted to the upper platen 32 and surrounds the aperture 33 therein. The chamber 34 is disposed such that the upper platen 32 is intermediate the lower platen 30 and the enclosed chamber 34.

Figure 4:
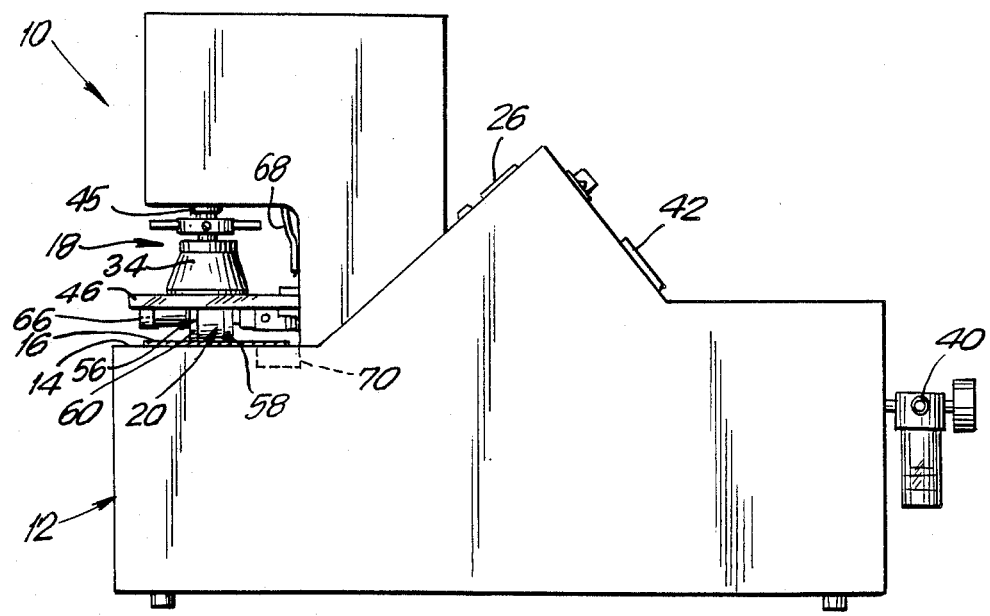
FIG. 4 is a side elevational view of the testing apparatus shown in FIG. 1.

A diaphragm 36 is mounted below the lower platen 30 and extends across the aperture 31 therein. A hydraulic chamber 38 is disposed below the diaphragm 36 and is in communication with a supply of hydraulic fluid through location 40 on the burst testing apparatus 10 as shown in FIG. 4. The burst testing apparatus 10 is operative to direct a flow of hydraulic fluid, such as glycerin, into the hydraulic chamber 38 to cause an increase in pressure and a corresponding expansion of the diaphragm 36 through the aperture 31 in the lower platen 30. The flow of hydraulic fluid may be caused by a motor having a movable piston in the hydraulic system.

The connection between the source of hydraulic fluid 40 and the hydraulic chamber 38 includes a hydraulic pressure sensing apparatus 42. The hydraulic pressure sensing apparatus 42 is operative to sense the hydraulic pressure in the system leading to the hydraulic chamber 38. Additionally, the hydraulic pressure sensing apparatus 42 is operative to generate a signal in response to a sensed decrease in hydraulic pressure that is indicative of a burst of the sheet material 16 presented to the burst testing apparatus 10. The hydraulic pressure sensing apparatus 42 is operatively connected to the control unit 22 to ensure that a signal identifying the sensed pressure level at the instant of the burst is sent to the control unit 22 for storage and subsequent analysis. The signal generated by the pressure sensing apparatus 42 in response to a burst also causes a valve or other such hydraulic pressure control means to decrease the hydraulic pressure, thereby preventing further expansion of the diaphragm 36.

The burst testing apparatus 10 further includes a clamp assembly 44 for driving a shaft 45 on which the enclosed chamber 34 and the upper platen 32 are mounted. The clamp assembly 44 comprises a pneumatic cylinder which is operative to selectively move the chamber 34 and the upper platen 32 toward or away from the lower plate 30. Additionally, the clamping assembly 44 is operative to automatically generate a preselected clamping pressure on the sheet 16 of test material disposed between the lower plate 30 and the upper platen 32. The clamping assembly 44 is operatively connected to other components of the testing apparatus 10 to respond to signals generated by the other components to achieve a required sequencing of movements of the chamber 34 and upper platen 32 toward or away from the lower platen 30. In particular, the clamping assembly 44 will lift the upper platen 32 away from the lower platen 30 in response to the signal generated by the pressure sensing means 42 indicating that a burst of the sample 16 has occurred. Additionally, the clamping assembly 44 will move the upper platen 32 down in response to other signals generated by the testing apparatus 10 as explained below.

A safety shield 46 is mounted in spaced generally parallel relationship to the lower platen 30. The safety shield 46 includes an aperture which permits the chamber 34 and the upper plate 32 to pass therethrough toward or away from the lower platen 30. The safety shield 46 preferably is formed from a transparent plastic material and is provided to ensure that the operator of the burst testing apparatus 10 does not inadvertently place his or her fingers in the vicinity of the moving components of the burst testing apparatus 10 during a testing procedure.

Figure 2:
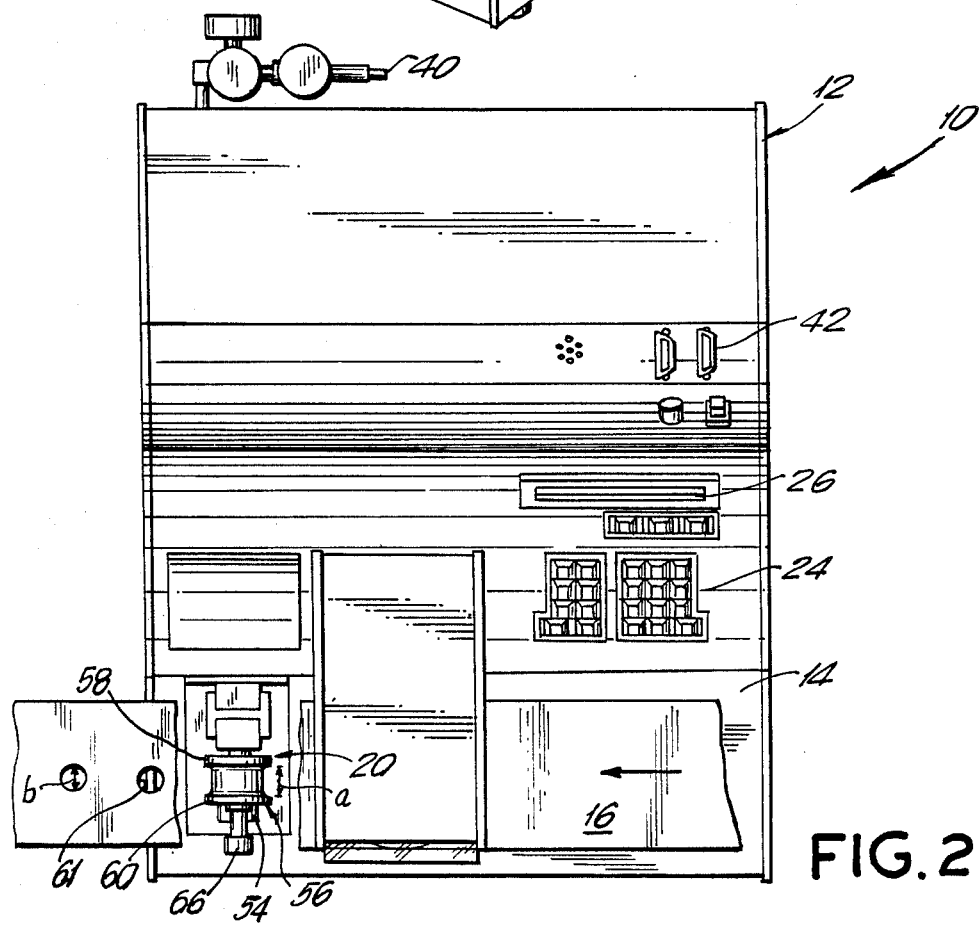
FIG. 2 is a top plan view of the testing apparatus shown in FIG. 1.
Figure 6:
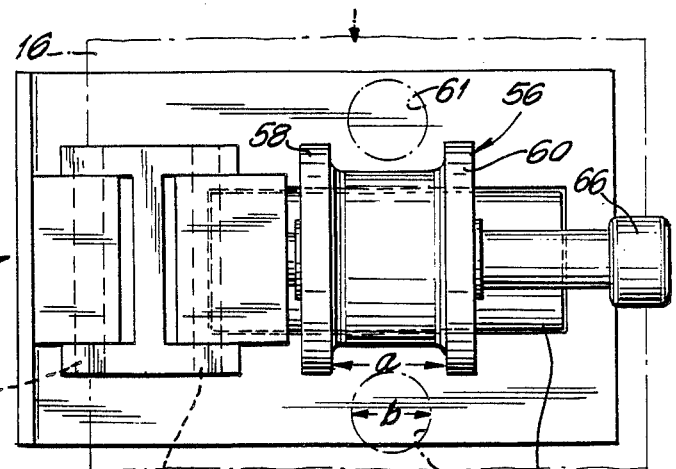
FIG. 6 is a top plan view of the drive apparatus shown in FIG. 5.
Figure 7:
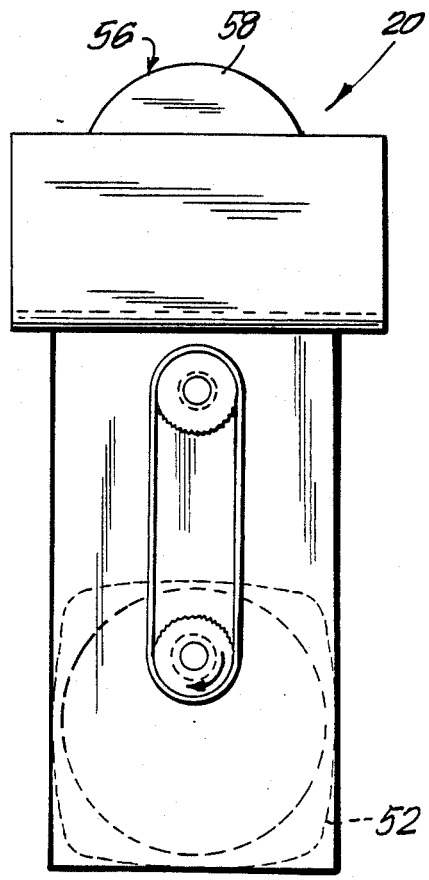
FIG. 7 is an end elevational view of the drive apparatus.
Figure 5:
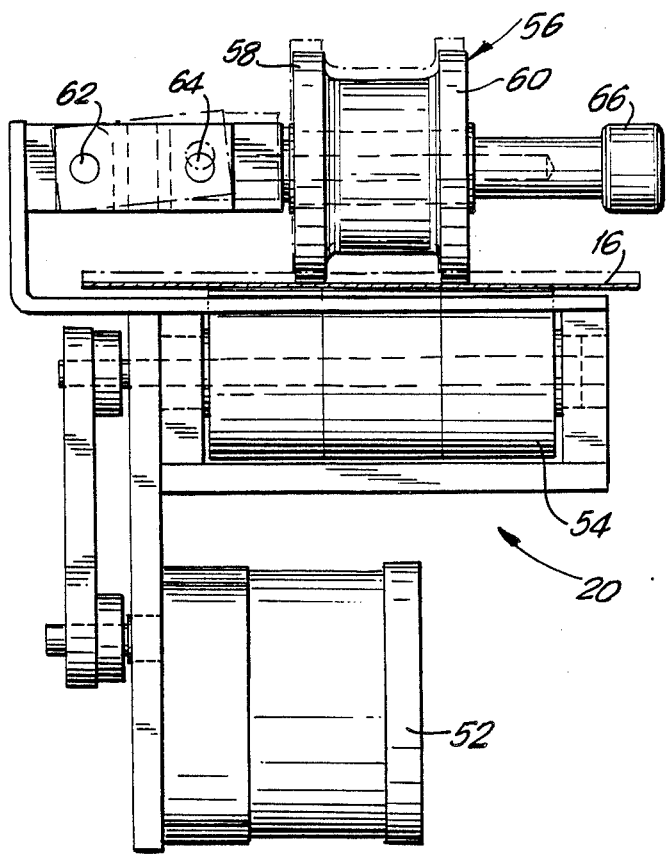
FIG. 5 is a front elevational view of the drive apparatus of the subject invention.

The burst testing apparatus 10 further includes a sheet feeder identified generally by the numeral 20 in FIGS. 1–3 and shown in greater detail in FIGS. 5–7. The sheet feeder 20 includes a motor 52 which is operatively connected to the control unit 22. The motor 52 includes switches which respond to signals generated elsewhere in the testing apparatus 10. Thus, the motor 52 may start after the clamping assembly 44 has lifted the upper platen 32 from the test sheet 16. However, the operation of the motor 52 may be subject to certain overriding instructions from the control unit 22 as explained herein. The motor 52 is connected to a drive roller 54 having a high friction surface which is effective for advancing the sheet material 16 along the surface 14 and past the registered apertures 31 and 33 in the lower and upper platens 30 and 32 respectively. The sheet material 16 is urged against the drive roller 54 by a weighted follower roller 56. The weighted follower roller 56 is freely rotatable about an axis extending generally parallel to the axis about which the drive roller 54 is rotatably driven. The weighted follower roller 56 includes a pair of spaced apart cylindrical contact surfaces 58 and 60 for contacting the surface of the sheet material 16. The distance "a" between the cylindrical contact surfaces 58 and 60 as shown in FIG. 6 is selected to exceed the maximum width "b" of the burst 61 that is likely to be created in the sheet material 16 as explained further herein.

The thickness of the sheet material 16 is likely to vary from one test to the next. As a result, the sheet feeder 50 must be able to accommodate sheet material 16 of varying thicknesses. Additionally, in certain tests, the sheet material 16 will be relatively small, and it will not be necessary or desirable to automatically feed the sheet material through the burst testing apparatus 10. As a result, the weighted follower roller 56 is mounted to the housing 12 of the burst testing apparatus 10 by a double hinge 62, 64 which, as shown most clearly in FIG. 5 enables the weighted follower roller 56 to be translated away from the drive roller 54 while still maintaining its axis parallel to the axis of the drive roller 54 and in contact with the top surface of the sheet 16. The weighted follower roller 56 further comprises a handle 66 mounted thereto to permit the entire weighted follower roller 56 to be rotated approximately 90° or more about the hinges 62, 64 for tests that will not require the automatic feeding of the sheet material 16.

As noted above the motor 52 which drives the drive roller 54 is operatively connected to the control unit 22. In particular, an operator can use the input controls 24 to render the motor 52 inoperative, and thus enable semi-automatic testing involving manual feeding of the sheet material 16. Alternatively, the operator can use the input control 24 to render the motor 52 operative for automatic feeding. Under these operating conditions, the motor 52 will start when the clamping assembly 44 lifts the upper platen 32. The motor 52 will operate to advance the sheet 16 a distance that may be established by the operator using the input controls 24.

The burst testing apparatus 10 further includes a photo-optical member 68 which is operative to direct a beam of light toward a reflective surface 70 and to sense the light reflected for surface 70. The photo-optical source 68 is operatively connected to the control unit 22 and generates a signal when the testing apparatus 10 is in the semi-automatic/manual feed mode and when the reflected light is not sensed. The photo-optical source 68 and the reflective surface 70 are disposed to be interrupted by the sheet of material 16 when the sheet 16 is in a position to be tested. The signal generated by the photo-optical source 68 will generate the clamp assembly 44 and the subsequent increase in hydraulic pressure after the specified clamping pressure has been achieved.

The procedure to the followed in employing the burst testing apparatus 10 will vary somewhat depending upon the size of the sample sheet 16 to be tested. If the test sample 16 is relatively small, the operator will rotate the weighted follower roller 56 approximately 90° away from the surface 14 to facilitate manual insertion of the test material 16 into the space between the surface 14 and the protective shield 46. The operator will also enter appropriate input data through the input controls 24 to indicate that the test material 16 will be manually fed. Other data entered through the input control 24 will include the indentity of the operator, the identity of the test sample and other test controls or parameters. The operator will proceed by urging the sheet of material 16 into the space between the lower platen 30 and the safety shield 46. The movement of the sheet material 16 between the photo-optical source 68 and the reflective surface 70 will generate a signal that will be sensed to actuate the clamping assembly 44 to urge the upper platen 32 and the enclosed chamber 34 downwardly toward the sheet material 24. This downward movement will generate a prespecified clamping force on the sheet material 16 between the lower platen 30 and the upper plate 32. Once the prespecified clamping force on the sheet material 16 has been achieved and the clamping motor is stopped, the hydraulic motor will activate the controlled flow of hydraulic fluid into the hydraulic chamber 38. The increasing hydraulic pressure will urge the diaphragm 36 through the aperture 31 in the lower platen 30 to thereby deform the test material 16 upwardly and through the aperture 33 in the upper platen 32. The amount of deformation of the sheet material 16 will increase as the hydraulic pressure increases. After a sufficient increase in the hydraulic pressure and a corresponding expansion of the diaphragm 36 through the apertures 31 and 33, the test material 16 will burst. The pressure at which this burst occurs will be sensed by the pressure sensing apparatus 42 and an appropriate signal identifying the burst pressure level will be received and recorded by the control unit 22. The hydraulic pressure sensing apparatus 42 will further reverse the flow of hydraulic fluid causing a reduction in the pressure in the hydraulic chamber 34. The clamp assembly 44 will respond to the reduction of hydraulic pressure by raising the upper platen 32, thereby enabling the operator to manually position the sheet material 16 for the next test. The movement of the sheet material 16 out of the burst test apparatus 10 and back into the burst test apparatus for the next test will be sensed by the photo-optical source 68. As a result, the testing sequence will proceed as explained above.

As noted previously, many of the sheets 16 of test material define elongated sheets on which more than 20 tests will be completed. For these tests, the operator will enter appropriate instructions into the input controls 24 to indicate that the burst testing apparatus 10 is to operate on an automatic feed mode. Here the operator will lift the weighted follower roller 56 upwardly and away from the drive roller 54 a sufficient amount to position the sheet material 16 therebetween. The operator will then enter appropriate instructions to initiate the testing process. The testing will proceed by the automatic clamping of the sheet material between the lower and upper platens 30 and 32 as explained above. Hydraulic fluid will then be directed into the hydraulic chamber 38 as explained in the previous example to generate a bursting of the clamped sample, with the burst pressure being stored for subsequent analysis. The pressure chamber accompanying the burst will be sensed, and the hydraulic fluid in the chamber 38 will be released. The sensed burst will also generate the release of the clamping pressure by the second platen 32 and will actuate the motor 52 and drive roller 54 to advance the sheet material 16 a selected amount to enable completion of the next test. The amount of advance of the sheet material 16 will vary depending upon the particular test material 16. In most instances the drive roller 54 will be operative to advance the test material 16 between 1.00 inch and 12.00 inches, with the typical advance being approximately 3.00 inches. The movement of the sheet material 16 under the action of the drive roller 54 is assured by the weighted follower roller 56 which achieves the required frictional engagement between the sheet material 16 and the drive roller 54. Additionally, the contact surfaces 58 and 60 of the weighted follower roller 56 are spaced sufficiently apart to ensure that the bursts 61 in the sheet material pass therebetween, with continuous frictional interaction being achieved by the weighted follower roller 56 and the drive roller 54. After the specified advanced of sheet material 16, the drive roller 54 will stop rotating and the clamp assembly 44 will urge the upper platen 32 and the enclosed chamber 34 downwardly and into the specified clamping engagement with the sheet material 16.

The automatic testing will proceed until the test sample 16 has been automatically advanced entirely through the burst testing apparatus 10. The completion of this testing may be sensed by the photo-optical source 68. The complete results of the test may be summarized on the digital display 26 and may be printed by the printer 28..The printed report will identify the operator, the test sample, the individual test reports and selected averages. A sample test report is set forth below.

REPORT DATE: 12-23-88
TEST/OPERATOR ID: JLS
SAMPLE ID: FOIL BACK
PRESSURE RANGE: 200 PSI    SAMPLE INTERVAL: 2 IN
TOTAL MEASUREMENTS: 10    UNITS: PSI
VALID READINGS: 10
LIMITS:
LOW NOT SET
HIGH NOT SET

| AVERAGE | STD. DEVIATION | HIGH | LOW |
|---------|----------------|------|-----|
| 27.4 | 1.9 | #3:31 | #9:24.4 |

| MEASUREMENT | BURST PRESSURE (PSI) | | | | |
|---|---|---|---|---|---|
| 1 | 25.4 | 27 | 31 | 28.2 | 26.8 |
| 6 | 26.5 | 29.3 | 26.8 | 24.4 | 28.2 |

In summary, a bust testing apparatus is provided for enabling automated burst testing of sheet material, and for ensuring consistent test conditions from one test to the next. The burst testing apparatus includes a burst tester having upper and lower platens with a clamp apparatus for automatically exerting a prespecified clamping pressure on a sheet of material disposed between the upper and lower platens. The burst testing apparatus further includes means for directing hydraulic fluid into a chamber, and for expanding a diaphragm into the sheet material being tested. Sufficient expansion of the diaphragm will cause a bursting of the sheet material, with the hydraulic pressure at the instant of the burst being sensed, stored and recorded. The flow of hydraulic fluid is reversed in response to the burst and the clamping pressure against the test sample is removed to enable the test sample to be advanced to a location for the next test thereon. The advancing of the test material from one test location to the next may be manual or may be automatic. The automatic advancement of the test material preferably is achieved by urging the test material between a drive roller and weighted hinged follower roller. Hinged mounting of the weighted follower roller enables the burst testing apparatus to accommodate test material of different respective thicknesses. A photo-optical source may be used to initiate and/or terminate the tests. The test results are displayed digitally on a screen and are printed by an associated printing apparatus.

While the invention has been described with respect to a preferred embodiment, it is apparent that various changes can be made without departing from the scope of the invention as defined by the appended claims.

We claim:

1. A burst testing apparatus for testing the burst strength of sheet material, said apparatus comprising:
   testing means for testing the burst strength of a sheet of material at a plurality of spaced apart locations thereon;
   feed means for automatically advancing the sheet material a preselected distance intermediate successive tests by the testing means;
   override means for rendering the feed means inoperative and enabling manual feeding of the sheet material into the burst testing apparatus; and
   sheet sensing means for sensing the presence of the sheet material in the burst testing apparatus and for generating a signal to initiate the testing after activation of the override means and after manual feeding of the sheet material.

2. A burst testing apparatus as in claim 1 further comprising control means for enabling adjustments to the distance by which the sheet is advanced by the feed means between successive tests.

3. A burst testing apparatus as in claim 1 wherein the sensing means comprises a photo-optical sensor.

4. A burst testing apparatus as in claim 1 wherein the feed means comprises thickness adjustment means for automatically enabling the feed means to apply uniform forces to sheet material of different thicknesses.

5. A burst testing apparatus as in claim 4 wherein the testing means comprises means for automatically clamping the sheet material to a prespecified clamping pressure prior to testing the burst strength thereof.

6. A burst testing apparatus as in claim 1 wherein the feed means comprises a generally cylindrical rotatable drive roller disposed to be gravitationally below the sheet of material, motor means for rotatably driving the drive roller, and a weighted follower roller rotatably mounted along an axis disposed gravitationally above the sheet of material for urging the sheet material into the drive roller, the axis of the weighted follower roller being movable relative to said drive roller for permitting passage of sheet material of different selected thicknesses therebetween.

7. A burst testing apparatus as in claim 6 wherein the weighted follower roller comprises a double hinge for permitting translation of said weighted follower roller relative to said drive roller.

8. A burst testing apparatus as in claim 6 wherein the weighted follower roller comprises a pair of spaced apart cylindrical contact surfaces the distance between said cylindrical contact surfaces exceeding the cross-sectional dimension of bursts created in the sheet material by the burst testing apparatus.

9. A burst testing apparatus for testing the burst strength of sheet material, said apparatus comprising:
   a generally horizontal support surface for supporting a sheet of material to be tested;
   testing means for testing the burst strength of the sheet of material on the support surface;
   a generally cylindrical rotatable drive roller disposed gravitationally below the sheet of material on the support surface and in frictional engagement with the sheet of material;
   motor means for selectively rotatably driving the drive roller;
   control means operatively connected to the motor means for alternately enabling automatic or semiautomatic operation of the testing apparatus such that during automatic operation of the testing apparatus the control means enables operation of the motor means after a test by the testing means for rotatably driving the drive roller and such that during semiautomatic operation of the testing apparatus the control means prevents the motor means from rotatably driving the drive roller; and
   a weighted follower roller rotatably mounted along an axis disposed gravitationally above the drive roller, said weighted follower roller comprising a double hinge for enabling said weighted follower roller to translate in an alignment generally parallel to the drive roller in response to different thicknesses of the sheet material passing therebetween and being rotatable away from the drive roller to enable semiautomatic operation of the testing apparatus.

10. A burst testing apparatus as in claim 9 further comprising sheet sensing means for sensing the presence of the sheet of material, said sheet sensing means being operatively connected to the control means for initiating the operation of the testing means during semiautomatic operation of the apparatus.

11. A burst testing apparatus as in claim 10 wherein the sheet sensing means is spaced from the testing means in a direction extending generally parallel to the longitudinal axis of the drive roller such that during semiautomatic operation of the apparatus, the sheet can be advanced into the apparatus in a direction extending parallel to the longitudinal axis of the feed roller.

* * * * *